United States Patent [19]
Cole et al.

[11] Patent Number: 5,527,310
[45] Date of Patent: Jun. 18, 1996

[54] MODULAR PELVIC FIXATION SYSTEM AND METHOD

[76] Inventors: J. Dean Cole, 500 Lakeview St., Orlando, Fla. 32804; Daniel F. Justin, 4544 Trescott Dr., Orlando, Fla. 32817

[21] Appl. No.: 269,823

[22] Filed: Jul. 1, 1994

[51] Int. Cl.⁶ .......................... A61B 17/68; A61B 17/84
[52] U.S. Cl. .............................. 606/60; 606/72
[58] Field of Search ................... 606/61, 60, 72, 606/69, 70, 71, 53, 54, 59; 403/378, 338

[56] References Cited

U.S. PATENT DOCUMENTS

| | | | |
|---|---|---|---|
| 4,616,949 | 10/1986 | Kellner | 430/373 |
| 4,794,918 | 1/1989 | Wolter | 606/72 |
| 5,306,275 | 4/1994 | Bryan | 606/61 |
| 5,342,361 | 8/1994 | Yuan et al. | 606/60 |
| 5,368,594 | 11/1994 | Martin et al. | 606/61 |

FOREIGN PATENT DOCUMENTS

| | | | |
|---|---|---|---|
| 9004948 | 5/1990 | WIPO | 606/61 |

*Primary Examiner*—Stephen C. Pellegrino
*Assistant Examiner*—Scott B. Markow
*Attorney, Agent, or Firm*—Allen, Dyer, Doppelt, Franjola & Milbrath

[57] ABSTRACT

An apparatus and method are provided for reducing, stabilizing, and fixating a pelvic ring fracture. The apparatus is a modular device that includes a plurality of clamps mountable to an exposed fractured pelvis with bone screws, at least one clamp on either side of the fracture. The clamps and the fracture are spanned by an elongated rod that is sufficiently pliable to be shaped to conform to the contours of the pelvis and sufficiently strong to stabilize and fixate the fracture. The method of treating the pelvic fracture includes affixing at least one clamp on each side of the fracture, cutting and shaping the rod, and securing the rod within the clamps to fixate the fracture. The modularity of the apparatus provides that the rod can be easily removed for reshaping as needed, and that the clamps can be easily removed for repositioning as needed.

8 Claims, 7 Drawing Sheets

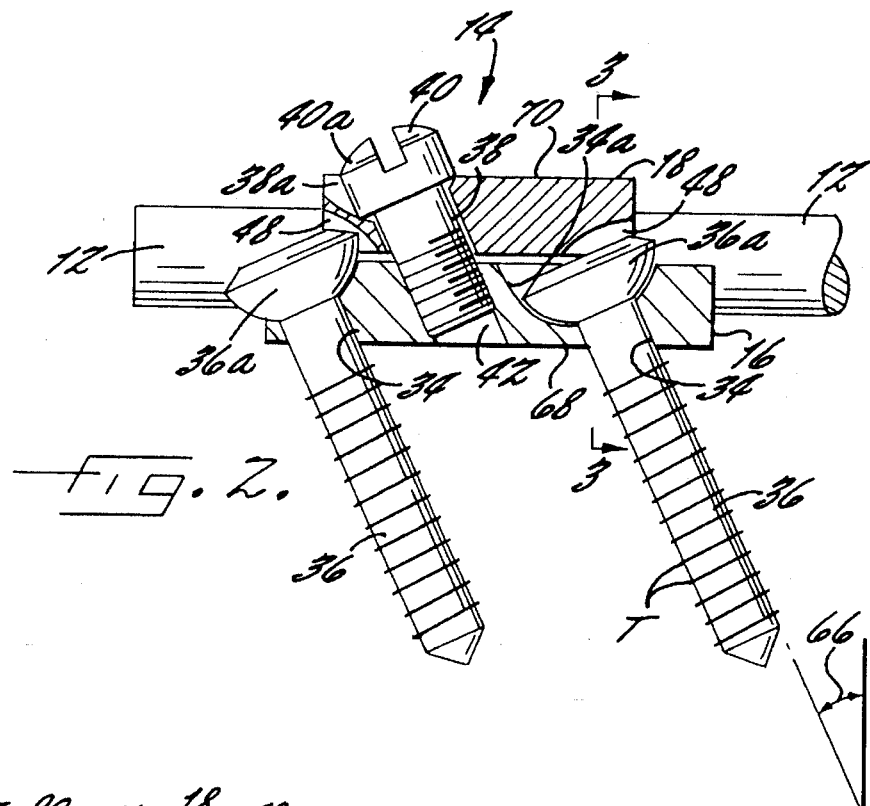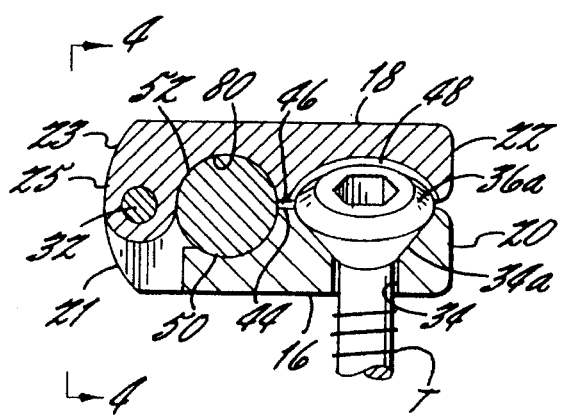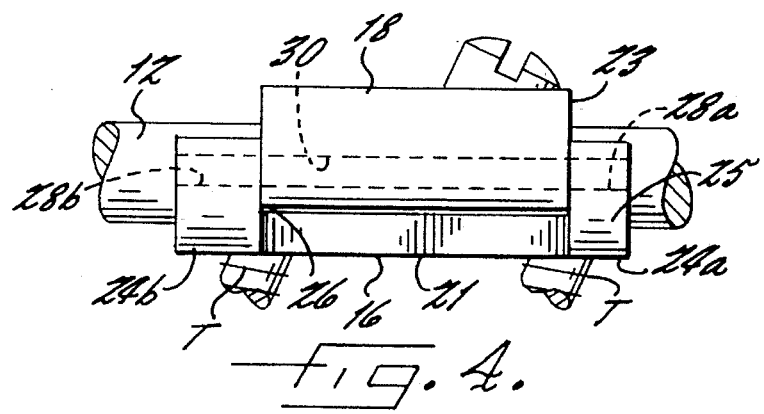

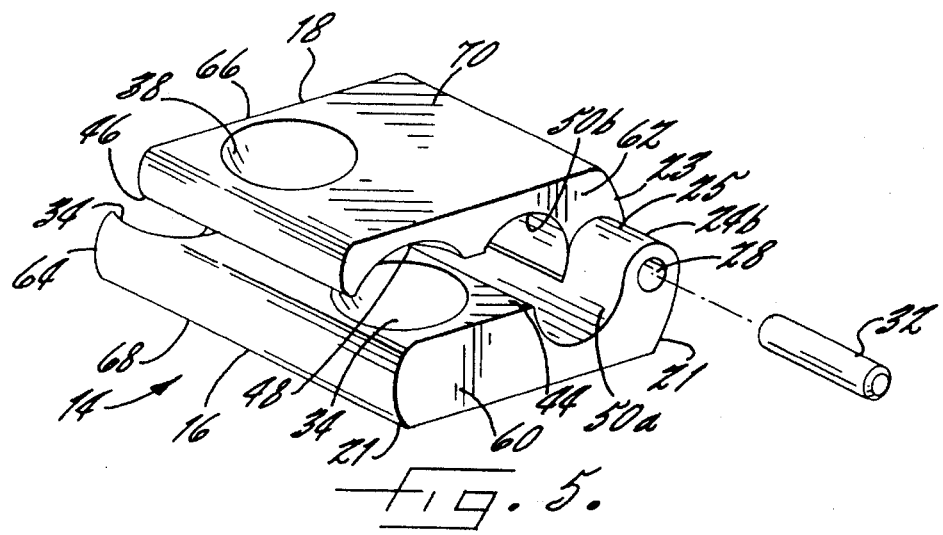
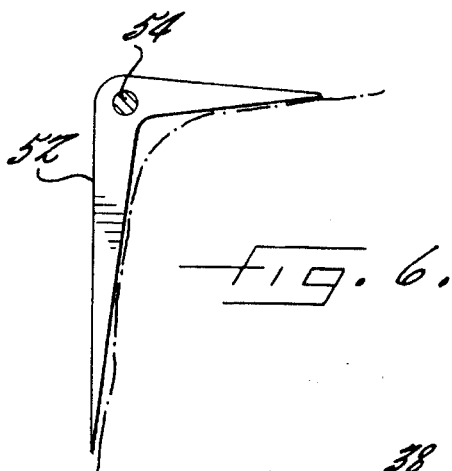
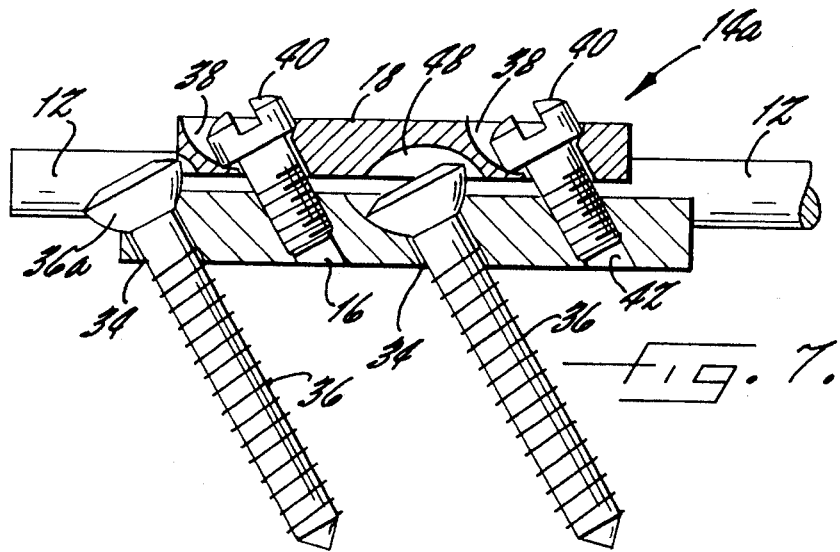

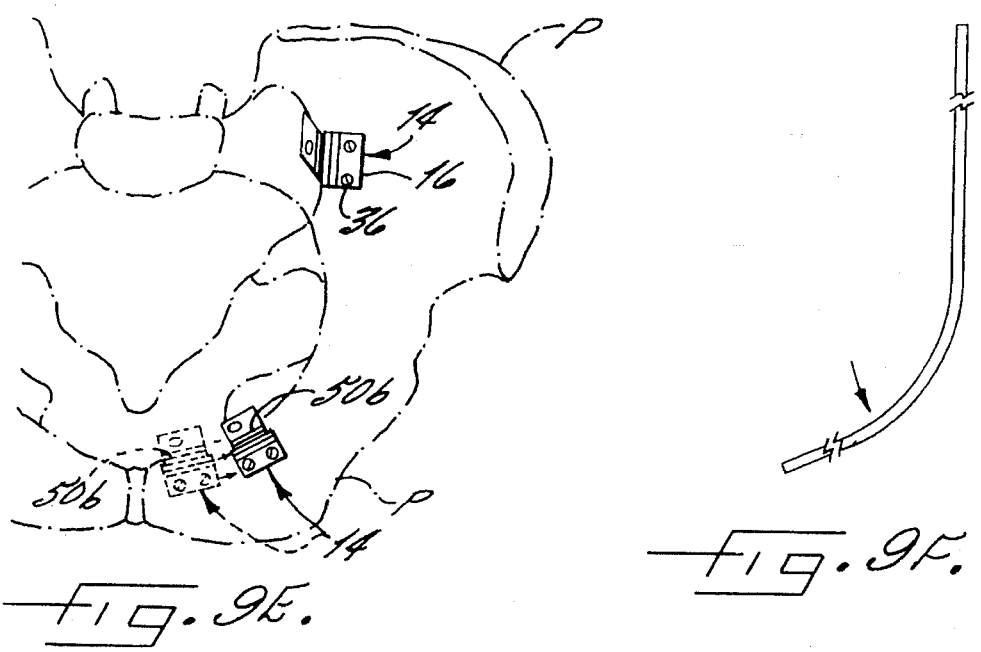
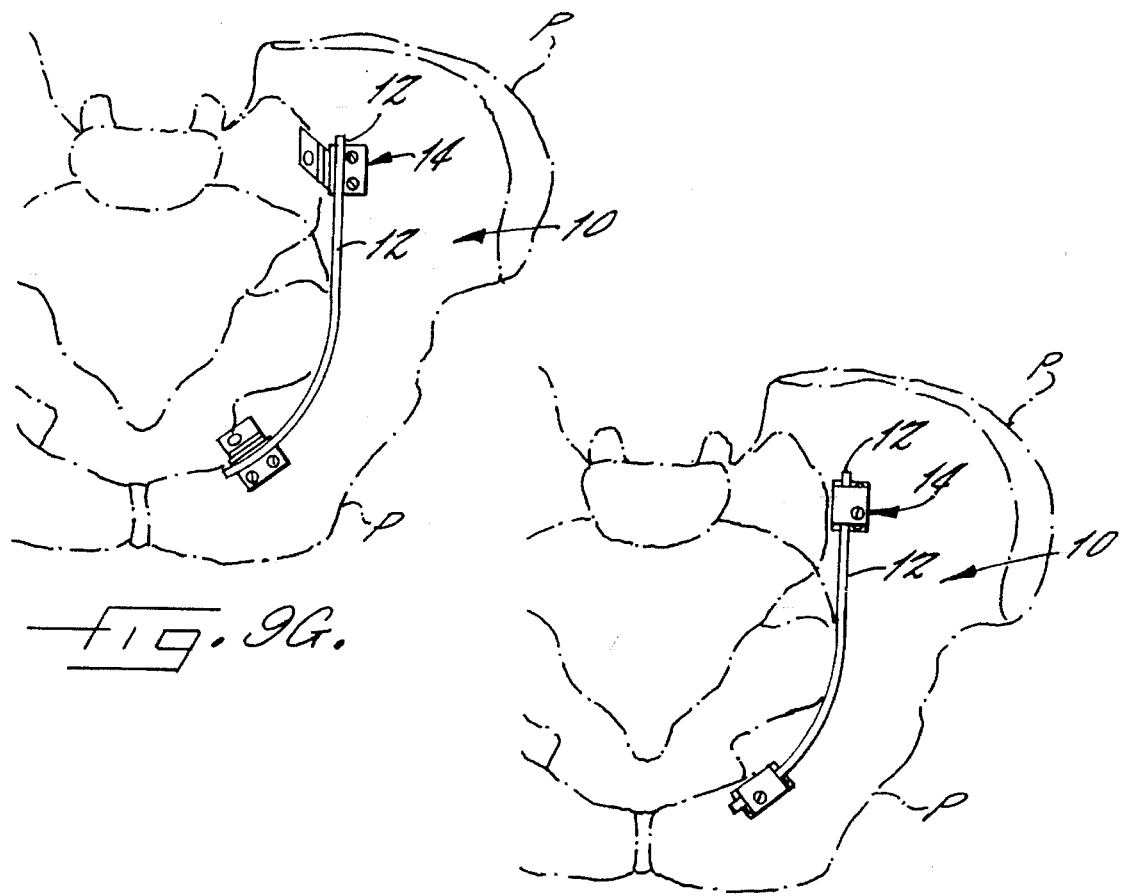

MODULAR PELVIC FIXATION SYSTEM AND METHOD

BACKGROUND OF THE INVENTION

1. Field of the Invention

The invention generally relates to an apparatus and method useful for the reduction, stabilization, and fixation of pelvic ring fractures, and more particularly, to a modular pelvic fixation apparatus that includes an elongated rod and a plurality of clamps mounted to an exposed fractured pelvis with bone screws.

2. Description of Related Art

Pelvic fractures, both with and without acetabular disruption, frequently require a procedure called open reduction and internal fixation. In this procedure an incision is made in a patient to expose the pelvic ring, and the pelvic bones are manipulated in order to stabilize the fracture. A metal plate is fastened to the bone with bone screws in order to stabilize and fixate or hold the fracture while healing takes place.

Fracture patterns in the acetabulum and pelvic area are widely varied and are often not uniform because the size and shape of these bones vary significantly from patient to patient. Because of the contours of these variably shaped bones, the metal plates used to stabilize and fixate the fractures must be bent and shaped to fit the bone.

A wide variety of internal bone plates are known in the art for fixation of bone fractures. These bone plates are generally mounted to the bone with some type of bone screw, and the surface of the plate that bears against the bone is generally flat or slightly curved. Some plates are formed as straight elongated plates and others are manufactured with a preformed contour to fit certain bone areas. However, few plates are shaped to fit fractures in the acetabulum area.

The contouring of straight plates must be done with extreme care, as the bending can weaken the plate and increase the risk of plate breakage. If a plate is very flexible, the region of the fracture is not sufficiently stabilized, and bone resorption in the fracture gap results due to movement. On the other hand, if the plate is very stiff, the plate takes up all the loading force. This creates an absence of functional loading on the bone, which may lead to general decay of the bone.

In many plates the screw holes are positioned within the main body of the bone plate, which limits the contouring of the plate. Some plates eliminate this problem by providing an elongated rod with screw tabs positioned along the side of the rod. However, the plates are still quite difficult to bend accurately, and contouring can be a time-consuming process when time is critical. Additionally, with this type of plate, as well as others, once a position is chosen for one of the screws, the place of the other screws is predetermined by the location of the screw holes. Also, once the plate is installed, if its position is found to be undesirable or inadequate reduction is obtained, all the screws must be removed and the holes redrilled to reposition the plate.

Thus it would be advantageous to have an internal pelvic fixation device that is strong enough to fix the fracture, but is easily contoured to the desired shape. It would also be advantageous to have as much freedom as possible in the placement of the fixation screws into the pelvis and to be able to change the position of the fixation device easily if the initial site chosen proves unsuitable or if inadequate reduction is obtained. It would additionally be advantageous to have a pelvic fixation system with a mechanism to address fractures of the acetabulum from the medial side.

SUMMARY OF THE INVENTION

It is thus an object of the present invention to provide a pelvic fixation device that is strong enough to fix a fracture, but is easily formed to the desired shape.

It is an additional object to provide a device that allows freedom of screw placement and ease in repositioning the device on the surface of the exposed pelvis.

It is a further object of the present invention to provide a mechanism for compressing fractures of the acetabulum from the medial side.

It is yet another object to provide a method of reducing, stabilizing, and fixating pelvic ring fractures.

The invention is directed to a novel internal pelvic fixation apparatus for treating fractures of a human pelvis. The fixation apparatus comprises an elongated rod and a plurality of clamps. The rod is sufficiently pliable to be shaped to conform to the contours of the pelvis. The rod is further sufficiently strong to stabilize and fixate a pelvic fracture. Each clamp is mounted on a selected surface area of the pelvis, typically with the use of a bone screw threaded through a bore in the clamp. Each clamp has an inner and an outer edge, a first and second side edge, and means for reversibly affixing the clamps to the rod.

In a preferred embodiment each clamp comprises an upper and a lower section, each section having an outer surface and a facing surface. Each facing surface has a recess extending from the first to the second side edge. The upper and lower sections are reversibly connectable to form a hole defined by the recesses. The hole is dimensioned to permit the rod to seat therein. In use, the clamps are generally positioned on opposite ends of the rod, and the assembly of the rod and clamps provides the internal reduction, stabilization, and fixation required in a fracture of the pelvis.

In a preferred embodiment, the upper and lower sections are hinged together in order to move relative to one another between an open and a closed position. The upper section has a bore extending from the outer surface to the facing surface. The bore is positioned between the recess and the outer edge. The lower section has a threaded bore extending from the facing surface and also has the bone screw bore extending from the facing surface to the outer surface. The threaded bore communicates with the bore in the upper section when the clamp is in the closed position. In use the elongated rod is affixed to a clamp by placing the clamp in the open position, positioning the rod within the recess in the lower section, and closing the clamp to encompass the rod within the hole formed by the recesses. Next a fastener such as a screw is inserted into the bore in the upper section and is screwed and tightened into the threaded bore in the lower section. Also in the preferred embodiment the bores are positioned at an angle relative to the lower section of the clamp in order to enable adequate purchase of the screws.

Given the arrangement described, it can be seen that the rod is selectively repositionable relative to a clamp and is further reshapable relative to the pelvis after an initial placement, which is a distinct advantage over previously disclosed arrangements.

In a preferred embodiment, the apparatus further comprises an angle bracket means that can be slidably mounted on the rod to provide compression from the medial side to a fracture in the acetabular region of an exposed pelvis. The angle bracket means comprises arms having an angle between them dimensioned to closely engage an acetabular region of the pelvis. The arms are generally normal to the long axis of the rod.

The method of utilizing the apparatus of the present invention comprises the steps of mounting a first clamp at a first desired location on an exposed surface of the pelvis on a first side of the fracture and mounting a second clamp at a second desired location on an exposed surface of the pelvis on a second side of the fracture. An elongated rod is then cut to a desired length for spanning the distance between the first and the second clamps. The rod is then shaped to a desired shape for reducing and fixing the fracture. Finally, the rod is secured within the first and the second clamps. If this initial placement and shaping are deemed inadequate, the rod may be removed from the clamps, repositioned and/or reshaped as needed, and resecured within the clamps.

A further embodiment of the method facilitates the shaping of the rod. In this embodiment a second, softer rod, insufficiently strong to support the fracture, may be shaped to conform to the targeted pelvic area and then used as a template against which to shape the first rod. This procedure would enable a more rapid and more accurate shaping of the rod.

The features that characterize the invention, both as to organization and method of operation, together with further objects and advantages thereof, will be better understood from the following description used in conjunction with the accompanying drawing. It is to be expressly understood that the drawing is for the purpose of illustration and description and are not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 2 is a partial cutaway front plan view of the invention of FIG. 1 looking along the sit line 2—2 shown in FIG. 1.

FIG. 3 is a partial cutaway end plan view of the invention of FIG. 2 looking along the site line 3—3 shown in FIG. 2.

FIG. 4 is a rear plan view of the invention of FIG. 2 looking along the site line 4—4 shown in FIG. 3.

FIG. 5 is a perspective view of the present invention.

FIG. 6 is a side plan view of an attachment to the invention of FIG. 1 looking along the sit line 5—5 shown in FIG. 1.

FIG. 7 is a partial cutaway front plan view of an alternate embodiment of the present invention.

FIGS. 9E–9H illustrate the method of reshaping and reattaching the device of the present invention.

DETAILED DESCRIPTION OF THE PREFERRED EMBODIMENT

A description of the preferred embodiments of the present invention will now be presented with reference to FIGS. 1–10.

Figure 1:
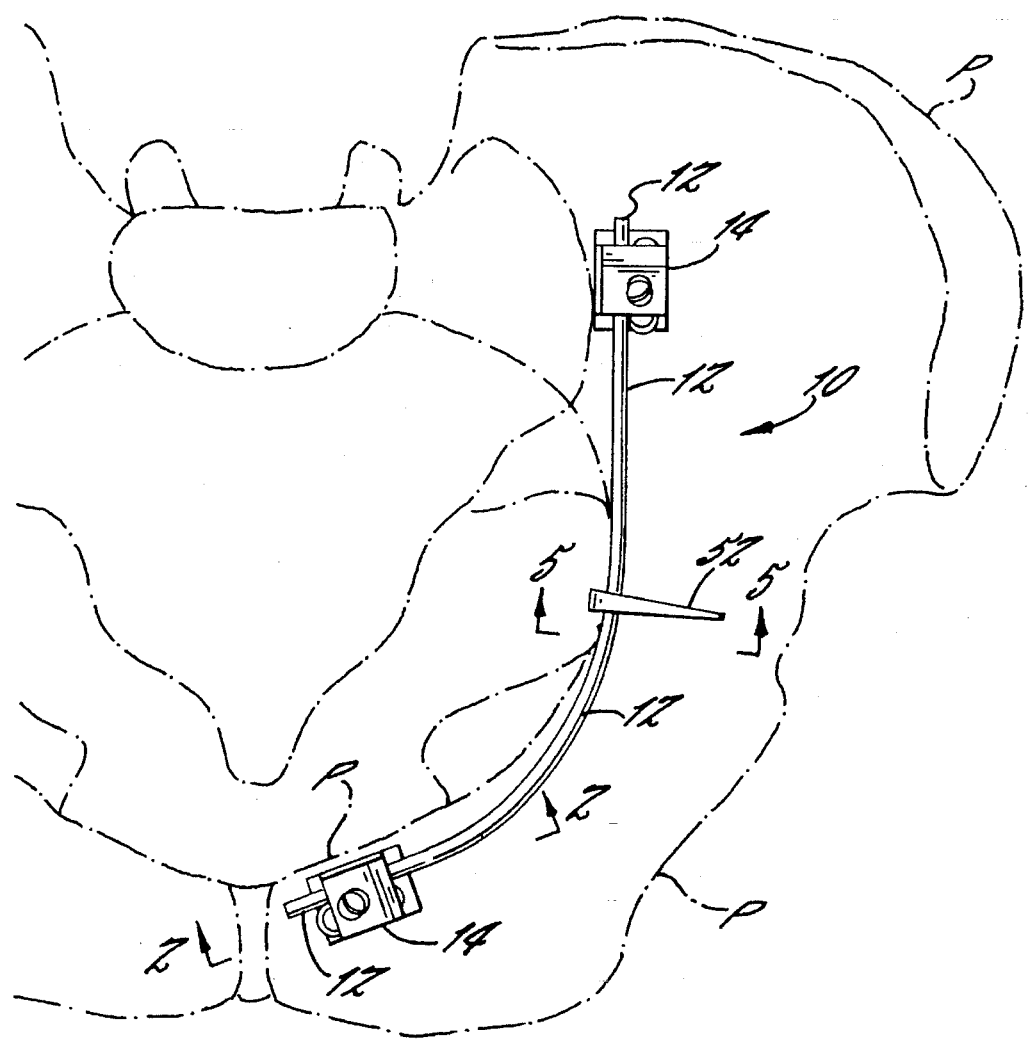
FIG. 1 is a perspective view of the present invention in use in an exposed human pelvis.

The present invention is directed to an internal pelvic fixation apparatus for use in treating a fracture of a human pelvis. In FIG. 1, a human pelvis, designated as P, has the preferred embodiment of a pelvic fixation apparatus 10 secured to the exposed pelvis P for reducing, stabilizing, and fixating a fracture of the pelvis P. The fixation apparatus 10 includes an elongated rod 12 and a plurality of clamps 14 for securing the fixation apparatus 10 to a selected surface of the pelvis P.

The elongated rod 12 is generally circular in cross section and is sufficiently pliable to allow for the bending and shaping required to conform the contours of a human pelvis. In a preferred embodiment, the rod 12 has a diameter in the range of 3–5 millimeters.

Each clamp 14 (see FIGS. 2–5) comprises a lower section 16 and an upper section 18. In a preferred embodiment, the lower section 16 is generally 0.65 inches long and 0.50 inches across, and the upper section 18 is generally 0.45 inches long and 0.50 inches across. The lower and upper sections 16, 18 each have an outer edge 20 and 22, respectively; an inner edge 21 and 23, respectively; first 60, 62 and second 64, 66 side edges, respectively; and an outer 68, 70 and a facing 44, 46 surface, respectively.

In a preferred embodiment, the inner edges 21, 23 of the lower and upper sections 16, 18 are connected by a hinge-type connection 25, as shown in FIGS. 3–5. The inner edge 23 of the upper section 18 is shaped to fit into a recess 26 formed between two opposed protrusions 24a, 24b in the inner edge 21 of lower section 16 (see FIG. 4). Pin openings 28a,b, oriented along the longitudinal axis of the clamp 14, are placed through the two opposed portions 24a,b, respectively. Another longitudinal pin opening 30 is placed through the inner edge 23 of the upper section 18 in alignment with the openings 28a,b. One or more pins 32 are inserted through the openings 28a,b, 30a,b, providing the hinge-type connection 25 that allows the lower and upper sections 16, 18 to move relative to one another between an open and closed position.

The lower section 16 of the clamp 14 includes at least one bone screw bore 34, and in a preferred embodiment, two bone screw bores 34, each extending from the facing surface 44 to the outer surface 68. Each bone screw bore 34 has a hemispherically shaped portion 34a in the facing surface 44 shaped to enable countersinking a bone screw 36 and its hemispherically shaped head portion 36a (FIG. 2). The bone screws 36 have bone-engaging threads T for securing the lower section 16 to the exposed surface of the pelvis P. The bone screw bores 34 are preferably positioned at about a 65° angle 66 relative to the adjacent surface of the pelvis P to enable adequate purchase of the bone screw 36 in the bone of the pelvis P.

The upper section 18 of the clamp 14 has at least one bore 38 extending from outer surface 70 to facing surface 68, dimensioned to receive a fastener, preferably a screw 40. The lower section 16 has a threaded bore 42, extending from facing surface 68, aligned with the bore 38 in the upper section 18, for receiving the screw 40 (FIG. 2). Each bore 38 has a widened portion 38a at the outer surface 70 shaped to receive the head 41a of screw 40. Screw 40 can be a machine screw, for example, with external threads. Threaded bore 42 has internal threads for engaging the external threads of the screw 40. In a preferred embodiment, the bores 38, 42 are positioned at an angle 66 of about 65° relative to the lower section 16 of clamp 14 surface so as to enable adequate purchase of the screw 40 when securing the lower 16 and upper 18 sections together.

The facing surface 46 of the upper section 18 has a recess 48 that aligns with each of the bores 34 in the lower section 16, as shown in FIGS. 2, 3, and 5. The recesses 48 provide clearance for the hemispherically shaped head 36*a* of the bone screws 36 so as to allow the upper and lower sections 16, 18 to be compressed together when the screw 40 is tightened in the bores 38 and 42.

In FIG. 5 corresponding recesses 50*a*, 50*b* are placed on the facing surfaces 44, 46 of the lower and upper sections 16, 18, respectively. In a preferred embodiment, the recesses 50*a,b*, which together form a hole 80 when the clamp 14 is in the closed position. Hole 80 conforms to the dimensions of the elongated rod 12 and is positioned generally between the inner edges 21, 23 and the bores 38, 42 of the sections 16, 18. The recesses 50*a,b* encompass the rod 12 between the lower and upper sections 16, 18 when the screw 40 compresses the sections 16, 18 together (FIG. 3). The clamps 14 are generally placed on opposite ends of the rod 12 when the fixation apparatus is mounted on the exposed surface of a fractured pelvis (FIG. 1).

An alternate embodiment of the fixation apparatus is shown in FIG. 7 where a pelvic fixation apparatus 14*a* includes two bores 38 in the upper section 18 for securing the upper section 18 to the lower section 16.

Figure 8:
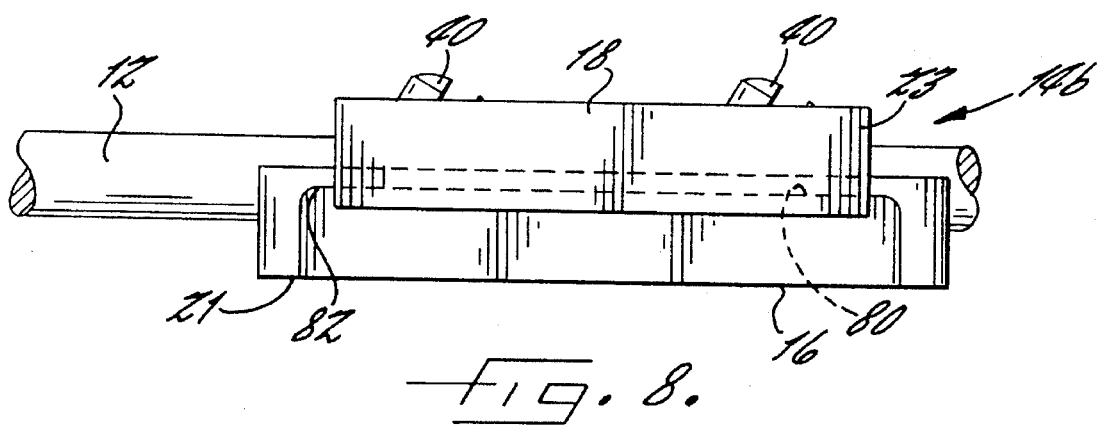
FIG. 8 is a rear plan view of an alternate embodiment of the present invention.
Figure 8A:
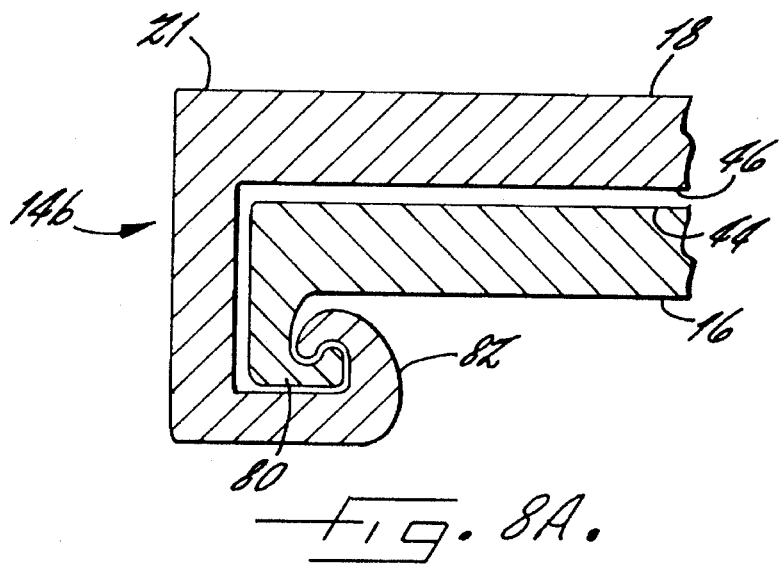
FIG. 8A is a side view of the connection between the upper and lower sections of this embodiment.
Figure 9A:
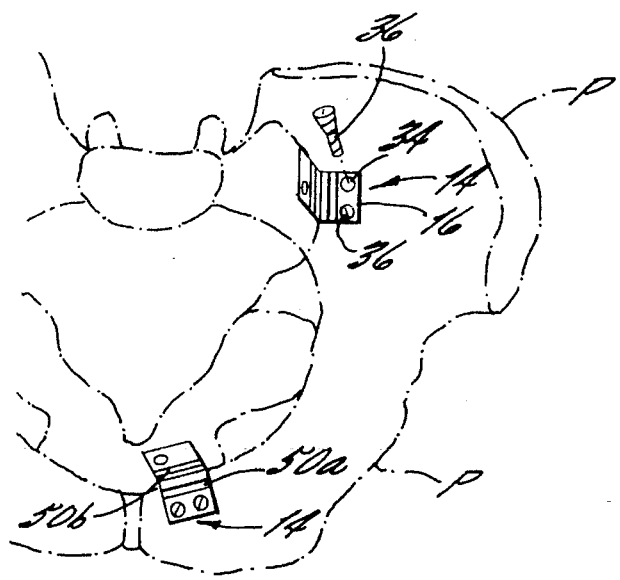
FIGS. 9A–9D are illustrations of the method of treating a pelvic fracture with the device of the present invention.
Figure 9B:
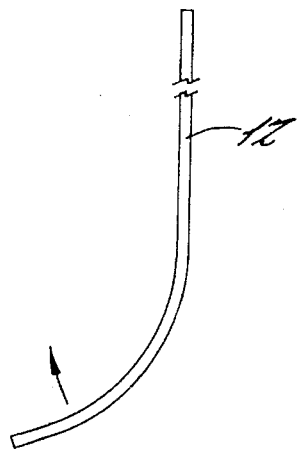
Figure 9C:
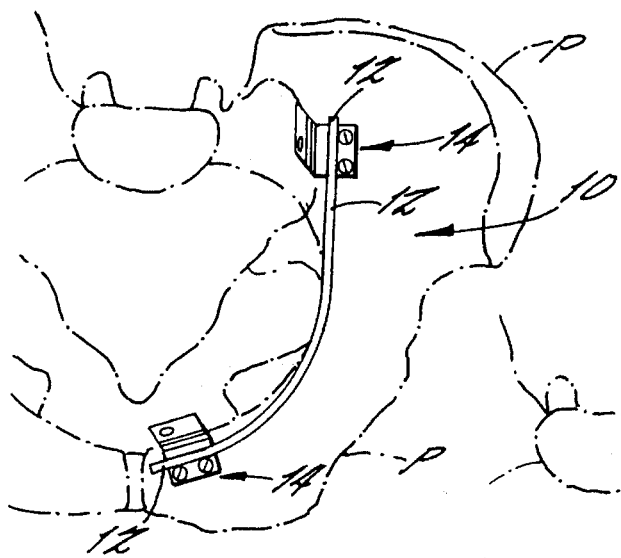
Figure 9D:
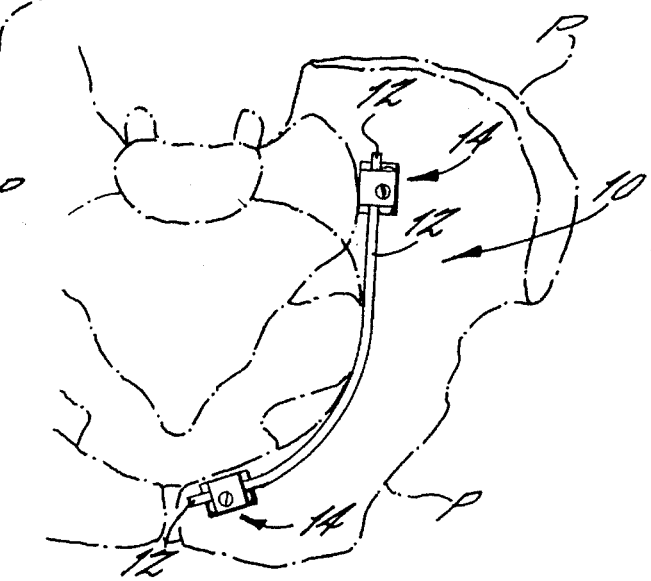
Figure 10A:
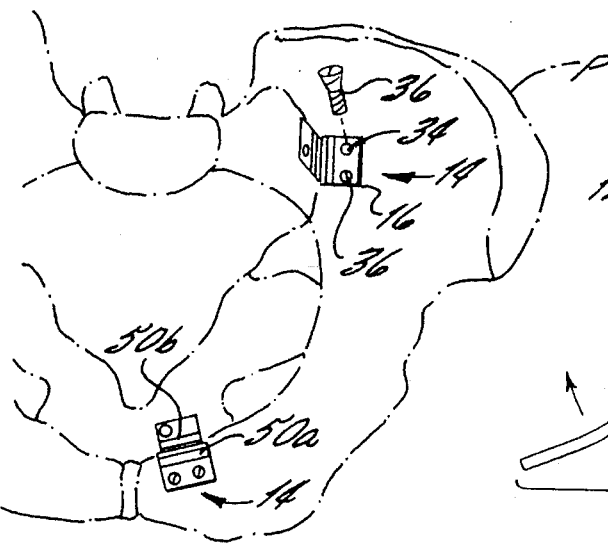
FIGS. 10A–10D illustrate the method of utilizing a second elongated rod as a template against which to form the first elongated rod for use in treating a pelvic fracture.
Figure 10B:
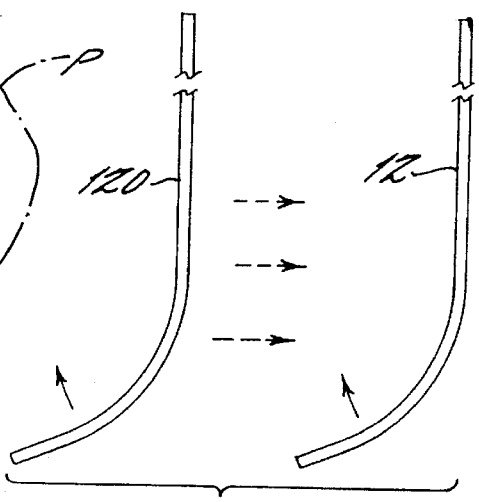
Figure 10C:
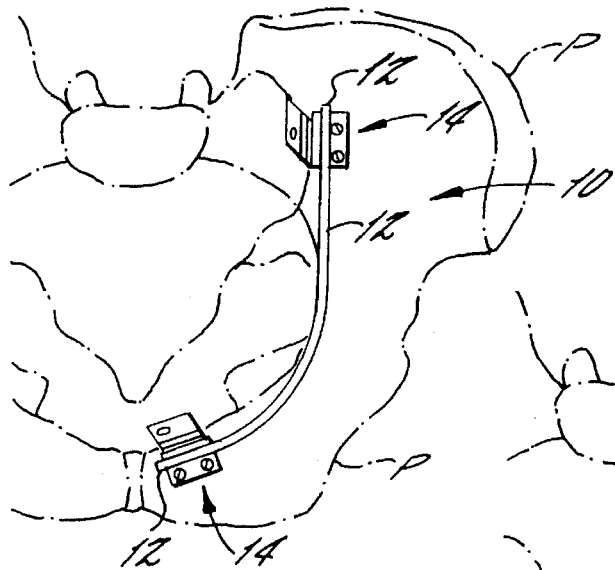
Figure 10D:
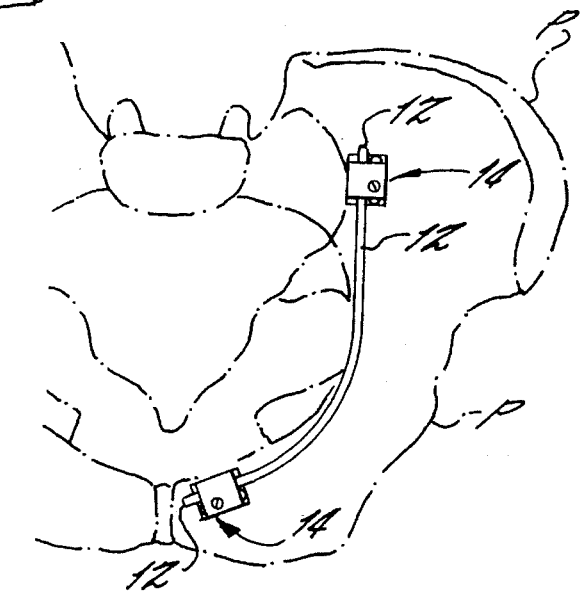

Another embodiment (FIG. 8) comprises a pelvic fixation apparatus 14*b* having an alternate connecting mechanism between the lower 16 and upper sections 18. In this embodiment the inner edge 21 of the lower section 16 has a ridge 80 along the outer surface 68 and the inner edge 23 of the upper section 18 has a lip 82 along the facing surface 46. The reversible connection is then formed by hooking the lip 82 of the upper section 18 under the ridge 80 of the lower section 16. This lip 82 and ridge 80 combination, the interaction of which is shown in FIG. 8A, replaces the hinge-type connection 25 discussed previously, the lip 82 hookable under the ridge 80 to form a reversible connection therebetween for permitting relative rotation along the inner edges 23,21 of the upper 18 and the lower 16 sections, respectively.

An angle bracket 52 with an opening 54 conforming to the diameter of the rod 12 can be slidably mounted on the rod 12 prior to securing the rod 12 in the clamps 14 (FIGS. 1 and 6). The angle bracket 52 provides for compression of fractures in the acetabular region from the medial side if a fracture pattern is in this portion of the pelvis P.

In a preferred embodiment, the rod 12, clamp 14, and angle bracket 52 are formed of a biocompatible material such as stainless steel or titanium.

The preferred method of use of the pelvic fixation apparatus 14 of the present invention, shown in FIG. 9(*a*)–(*d*), allows for greater freedom of both clamp and screw placement due to the modularity of the rod 12 and clamps 14. A first and a second clamp 14 are mounted at a first and a second desired location, on, respectively, a first and a second side of the fracture in the pelvis P with bone screws 36 placed through the bores 34 in the lower sections 16 of the clamps 14 [FIG. 9(*a*)]. The rod 12 is then cut to a desired length for spanning the distance between the first and the second clamps 14 [FIG. 9(*b*)]. Next the rod 12 is bent to the desired length and shaped to reduce and fix the fracture [FIG. 9(*b*)]. The contoured rod 12 is then placed between the recesses 50*a,b* in the lower and upper sections 16, 18 of the clamps 14 and the sections 16, 18 are closed. The screws 40 are placed into the bores 38, 42 and tightened in order to compress the lower and upper sections 16, 18 together, securing the rod 12 in place between the sections 16, 18 of the clamps 14.

If the fixation apparatus 10 is not positioned correctly, one or both of the clamps 14 can be easily removed and repositioned [FIG. 9(*e*)]. If the rod 12 needs to be reshaped or shortened, it can be easily removed from the clamps 14, rebent, and replaced [FIG. 9(*f*)] without having to reposition the clamps 14 on the exposed pelvis P. Of course, both of these procedures can occur if necessary.

Another embodiment of the method of utilizing the apparatus 10 of the present invention, shown in FIG. 10(*a–d*), comprises cutting and shaping a second, softer elongated rod 120 to conform to the pelvic area to be fixated and then using the second rod 120 as a template in comparison to which the first elongated rod 12 is cut and shaped. This method can enable a more rapid and accurate installation of device 10.

The present invention provides an internal pelvic fixation apparatus that is strong enough to stabilize and fix pelvic fractures while also being easily contoured to perform to the desired shape of the pelvis. The invention also allows freedom of clamp and screw placement while allowing for easy removal and repositioning. The apparatus also offers a mechanism for compressing fractures of the acetabulum from the medial side.

It may be appreciated by one skilled in the art that additional embodiments may be contemplated, including the use of analogous implements in the reduction and stabilization of other bones than the pelvis.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An internal pelvic fixation apparatus for use in treating a fracture of a pelvis, the apparatus comprising:

a unitary elongated rod sufficiently pliable to be shaped to conform to the contours of a pelvis and sufficiently strong to stabilize and fixate a pelvic fracture and further sufficiently long to span the fracture when affixed thereacross;

a plurality of clamps, each clamp having an inner edge, an outer edge, a first and a second side edge, means for reversibly affixing the clamp to the elongated rod, and means distinct from the affixing means for mounting each clamp to a selected surface area of the pelvis, the plurality of clamps comprising a first and a second clamp mountable to a first and a second side, respectively, of the fracture, the elongated rod thereby affixable in spanning relation to the fracture by affixing the elongated rod to the first and the second clamps, wherein each clamp has a bone screw bore therein and the means for mounting comprises the bone screw bore which is adapted to receive a screw to attach to the pelvis, and wherein each clamp comprises a lower section and an upper section, each section having an outer surface and a facing surface having a recess therein extending from the first to the second side edge, the lower and the upper sections reversibly connectable to form a hole defined by the recesses, the hole dimensioned to permit the elongated rod to seat therein; and hinge means, wherein the lower and the upper sections of each clamp are reversibly connected by the hinge means along the inner edge, thereby permitting the lower and the upper sections to be moved between an open and a closed position.

2. The apparatus recited in claim 1, wherein:

the upper section of each clamp has a bore extending from the outer surface to the facing surface, the bore positioned between the recess and the outer edge;

the lower section has a threaded bore extending from the facing surface, the threaded bore communicating with the bore in the upper section when each clamp is in the closed position; and the means for affixing each clamp to the elongated rod comprises the upper section bore and the lower section threaded bore, which are adapted to receive a screw threthrough when each clamp is in the closed position with the elongated rod seated therein.

3. The apparatus recited in claim 2, wherein the bone screw bore is positioned in the lower section of each and extends from the facing surface to the outer surface.

4. The apparatus recited in claim 3, wherein the bone screw bore is positioned at an angle relative to the lower section of each to enable adequate purchase of the bone screw within the pelvis.

5. The apparatus recited in claim 3, wherein the upper section of each further has a bone screw recess in the facing surface of the upper section positioned opposite the bone screw bore for providing clearance for a head of a bone screw.

6. The apparatus recited in claim 5, wherein the bore in the upper section has a widened portion at the outer surface for countersinking a screw.

7. An internal pelvic fixation apparatus for use in treating a fracture of a pelvis, the apparatus comprising:

a unitary elongated rod sufficiently pliable to be shaped to conform to the contours of a pelvis and sufficiently strong to stabilize and fixate a pelvic fracture and further sufficiently long to span the fracture when affixed thereacross;

a plurality of clamps, each clamp having an inner edge, an outer edge, a first and a second side edge, means for reversibly affixing the clamp to the elongated rod, and means distinct from the affixing means for mounting each clamp to a selected surface area of the pelvis, the plurality of clamps comprising a first and a second clamp mountable to a first and a second side, respectively, of the fracture, the elongated rod thereby affixable in spanning relation to the fracture by affixing the elongated rod to the first and the second clamps, wherein each clamp has a bone screw bore therein and the means for mounting comprises the bone screw bore through which is adapted to receive a screw to attach to the pelvis, and wherein each clamp comprises a lower section and an upper section, each section having an outer surface and a facing surface having a recess therein extending from the first to the second side edge, the lower and the upper sections reversibly connectable to form a hole defined by the recesses, the hole dimensioned to permit the elongated rod to seat therein; and wherein:

the inner edge of the lower section has a ridge along the outer surface;

the inner edge of the upper section has a lip along the facing surface, the lip hookable under the ridge to form a reversible connection therebetween for permitting relative rotation along the inner edges of the upper and the lower sections.

8. An internal pelvic fixation apparatus for use in treating a fracture of a patient's pelvis, comprising:

an elongated rod having a generally circular cross section and a diameter in the range of 3 to 5 millimeters, the elongated rod being sufficiently pliable to be shaped to conform to the contours of a pelvis and sufficiently strong to stabilize and fixate a pelvic fracture and further sufficiently long to span the fracture when affixed thereacross; and a pair of clamps comprising a first and a second clamp, each clamp having an inner edge, an outer edge, and a first and a second side edge, and each clamp comprising:

hinge means;

a lower section and an upper section, each section having an outer surface and a facing surface having a rod recess therein extending from the first to the second side edge, the lower and the upper sections connected to the hinge means along the inner edges, thereby permitting the lower and the upper sections to be moved between an open and a closed position, the rod recesses forming a hole when the clamp is in the closed position, the hole dimensioned to permit the elongated rod to seat therein, the lower section further having two parallel bone screw bores therein for mounting the clamp to a selected surface area of the pelvis with a bone screw, the bone screw bores positioned at an angle relative to the lower section of each clamp to enable adequate purchase of the bone screw, the upper section of each clamp further having a pair of bone screw recesses in the facing surface of the upper section positioned opposite the bone screw bores for providing clearance for a head of each bone screw, the upper section further having two parallel bores extending from the outer surface to the facing surface, the bores in the upper section positioned between the rod recess and the outer edge and each having a widened portion at the outer surface adapted for countersinking a screw, the lower section further having two parallel threaded bores extending from the facing surface, the threaded bores communicating with the bores in the upper section when each clamp is in the closed position; and an angle bracket having a pair of arms having an angle therebetween dimensioned to closely engage an acetabular region of a pelvis, the angle bracket slidably mounted on the elongated rod with the arms generally normal to the elongated rod for compressing a fracture of an acetabular region of an exposed pelvis;

wherein in use the lower sections of the first and the second clamps are mountable on a first and a second side of the fracture, respectively, each clamp affixable to the elongated rod by positioning the rod within the rod recess in the lower section of each clamp with each clamp in the open position, each clamp movable to the closed position to encompass the elongated rod within the hole formed by the rod recesses, each bore adapted to receive a screw in the upper section of each clamp body, each threaded bore in the lower section of each clamp body is adapted to receive the screw, a tightening of the screw for securing the elongated rod to position the elongated rod in spanning relation to the fracture.

* * * * *